(12) United States Patent
Zhou et al.

(10) Patent No.: US 10,913,070 B2
(45) Date of Patent: Feb. 9, 2021

(54) MICROARRAY CARRIER ASSEMBLY

(71) Applicant: Centrillion Technologies Taiwan Co. LTD., Hsinchu County (TW)

(72) Inventors: Wei Zhou, Palo Alto, CA (US); Lin-Hsin Tu, Hsinchu County (TW); Yao-Kuang Chung, Hsinchu County (TW); Tzu-Kun Ku, Hsinchu County (TW); Glenn McGall, Palo Alto, CA (US)

(73) Assignee: Centrillion Technologies Taiwan Co. LTD., Hsinchu County (TW)

( * ) Notice: Subject to any disclaimer, the term of this patent is extended or adjusted under 35 U.S.C. 154(b) by 189 days.

(21) Appl. No.: 15/993,626

(22) Filed: May 31, 2018

(65) Prior Publication Data
US 2018/0345290 A1 Dec. 6, 2018

Related U.S. Application Data

(60) Provisional application No. 62/512,739, filed on May 31, 2017.

(51) Int. Cl.
*B01L 9/00* (2006.01)
*C12N 15/10* (2006.01)

(52) U.S. Cl.
CPC .......... *B01L 9/523* (2013.01); *C12N 15/1093* (2013.01); *B01L 2300/0819* (2013.01)

(58) Field of Classification Search
CPC .... B01L 9/523; B01L 9/52; B01L 9/00; B01L 2300/0819; B01L 2300/0809; B01L 2300/08; C12N 15/1093; C12N 15/102; C12N 15/10; C12N 15/09
USPC .......................................................... 422/62
See application file for complete search history.

(56) References Cited

U.S. PATENT DOCUMENTS

2016/0193608 A1* 7/2016 Isami ................ B29C 66/30223
436/501

* cited by examiner

*Primary Examiner* — Christine T Mui
(74) *Attorney, Agent, or Firm* — JCIPRNET

(57) ABSTRACT

A microarray carrier assembly including a scan tray and a plurality of microarray blocks detachably disposed on the scan tray is provided. The scan tray includes a frame including an opening and a slot, and a transparent substrate covering the opening of the frame. Each of the microarray blocks includes a main body, a probe array distributed on the main body and facing towards the transparent substrate of the scan tray, and a plurality of guiding pins disposed on the main body and surrounding the probe array, wherein a top surface area of the guiding pin opposite to the main body is less than a bottom surface area of the guiding pin connected to the main body, and the guiding pins are detachably inserted into the slot of the frame of the scan tray.

20 Claims, 8 Drawing Sheets

MICROARRAY CARRIER ASSEMBLY

CROSS-REFERENCE TO RELATED APPLICATION

This application claims the priority benefit of U.S. provisional application Ser. No. 62/512,739, filed on May 31, 2017. The entirety of the above-mentioned patent application is hereby incorporated by reference herein and made a part of this specification.

BACKGROUND

Technical Field

The invention relates generally to a sample carrier assembly for use in biotechnology applications, in particular, to a microarray carrier assembly used in biomolecular assays.

Description of Related Art

Microarray technology has been developing quickly and widely used in the study of genetics, proteomics, pharmaceutical research, clinical detection etc. In addition, due to the recent demand for high-throughput assays, high density microarrays have been developed on which several hundred thousand probes are immobilized. However, conventional array plates do not allow for customized high throughput applications because conventional microarray plates come in standard format, and each conventional microarray plate only allows for a single assay. It is a time-consuming process to run the assay many times using the conventional microarray plates for multiplexing assay formats. As a result, there is a need for a customized high-throughput microarray carrier which allows for concurrently processing multiple assay formats.

SUMMARY

The disclosure provides a microarray carrier assembly which allows for high-throughput by accommodating multiple microarray blocks on a single scan tray, thereby concurrently processing customized assay formats.

The disclosure provides a microarray carrier assembly including a scan tray and a plurality of microarray blocks detachably disposed on the scan tray. The scan tray includes a frame including an opening and a slot, and a transparent substrate covering the opening of the frame. Each of the microarray blocks includes a main body, a probe array distributed on the main body and facing towards the transparent substrate of the scan tray, and a plurality of guiding pins disposed on the main body and surrounding the probe array, wherein a top surface area of the guiding pin opposite to the main body is less than a bottom surface area of the guiding pin connected to the main body, and the guiding pins are detachably inserted into the slot of the frame of the scan tray.

The disclosure provides a microarray carrier assembly including a scan tray and at least one microarray block detachably assembled to the scan tray. The microarray block includes a main body having a first side and a second side opposite to the first side, a probe array distributed on the first side of the main body and including a plurality of pillars and biochips bonded thereon, and a guiding pin disposed on a periphery of the first side of the main body. The scan tray includes a frame comprising an opening and a slot, and a transparent substrate covering the opening of the frame. The guiding pin of the at least one microarray block is detachably inserted into the slot of the frame, and a maximum height of the guiding pins combing with a gap between the guiding pin and a bottom surface of the slot minus a height of the probe array is a first height, and the first height is greater than a thickness of one of the biochips.

Based on the above, the microarray carrier assembly includes at least one microarray block detachably disposed on the scan tray. Each microarray block includes a probe array, and the quantity of the probe array can be customized. Moreover, a plurality of microarray blocks can be assembled onto the scan tray and the block holder, and each microarray block can be a different assay such that the scan tray and the block holder carries multiple assays on these microarray blocks. Therefore, the user can run the multiple assays at the same time using these microarray blocks. In addition, the maximum height of the guiding pin is higher than the probe array to prevent contamination. Furthermore, the microarray blocks can be easily separated from the block holder using the unloading plate.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

The detailed description set forth below is intended as a description of the presently exemplary device provided in accordance with aspects of the disclosure and is not intended to represent the only forms in which the disclosure may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

Figure 1A:
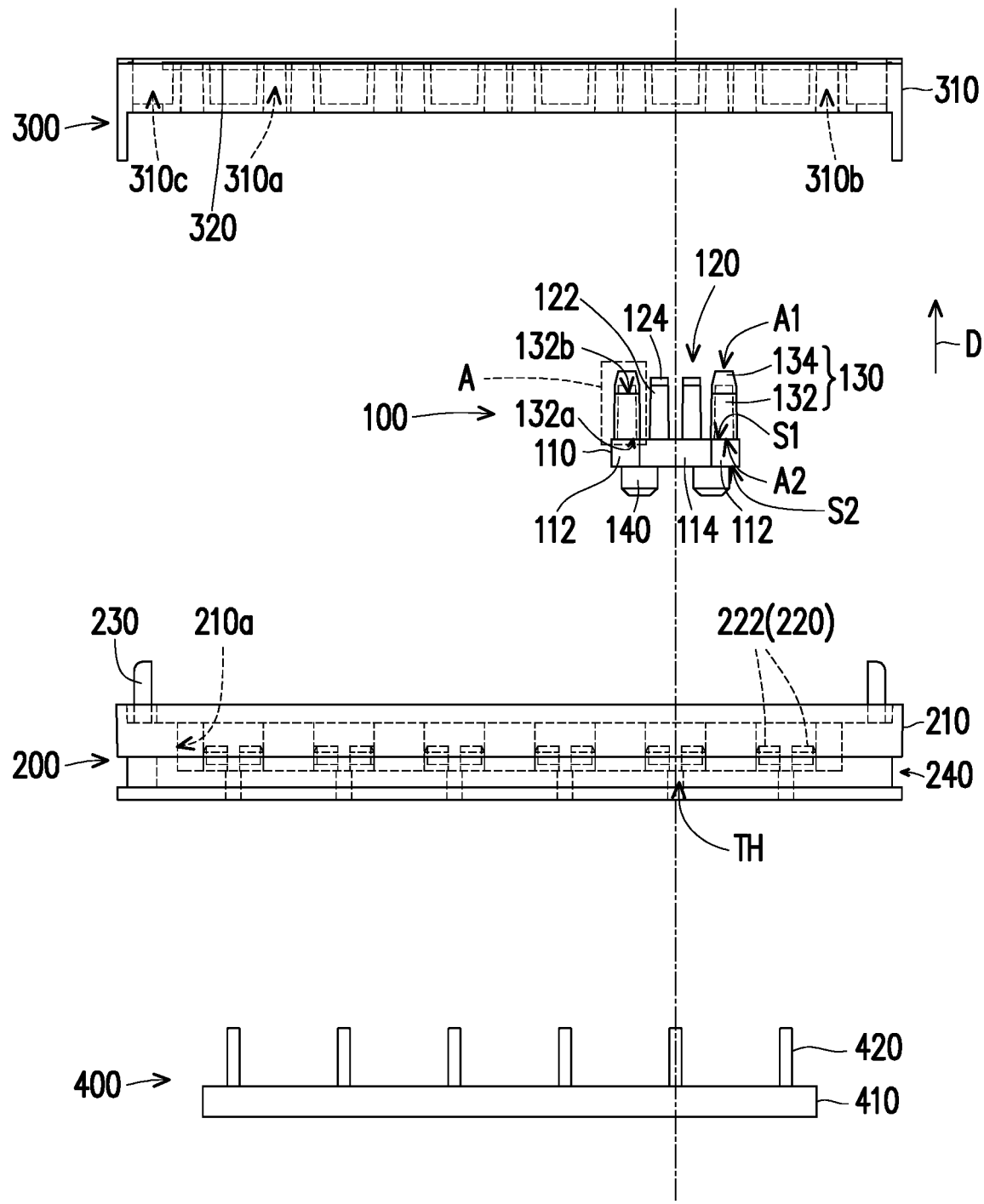
FIG. 1A is a schematic exploded side view of a microarray carrier assembly according to an embodiment of the disclosure.
Figure 1B:
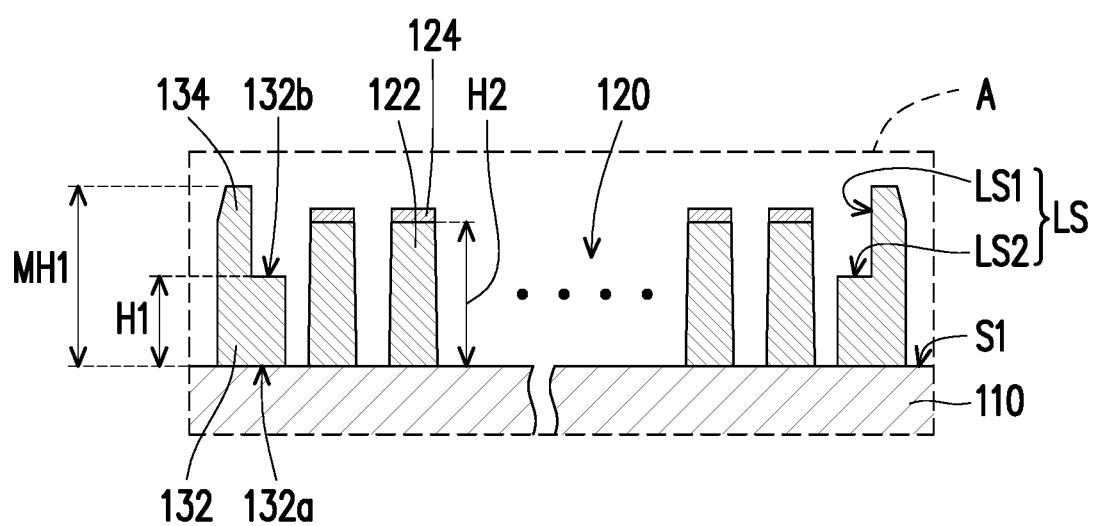
FIG. 1B is a schematic cross sectional view of the dashed box A indicated in FIG. 1A along a length direction of a microarray block according to an embodiment of the disclosure.
Figure 2A:
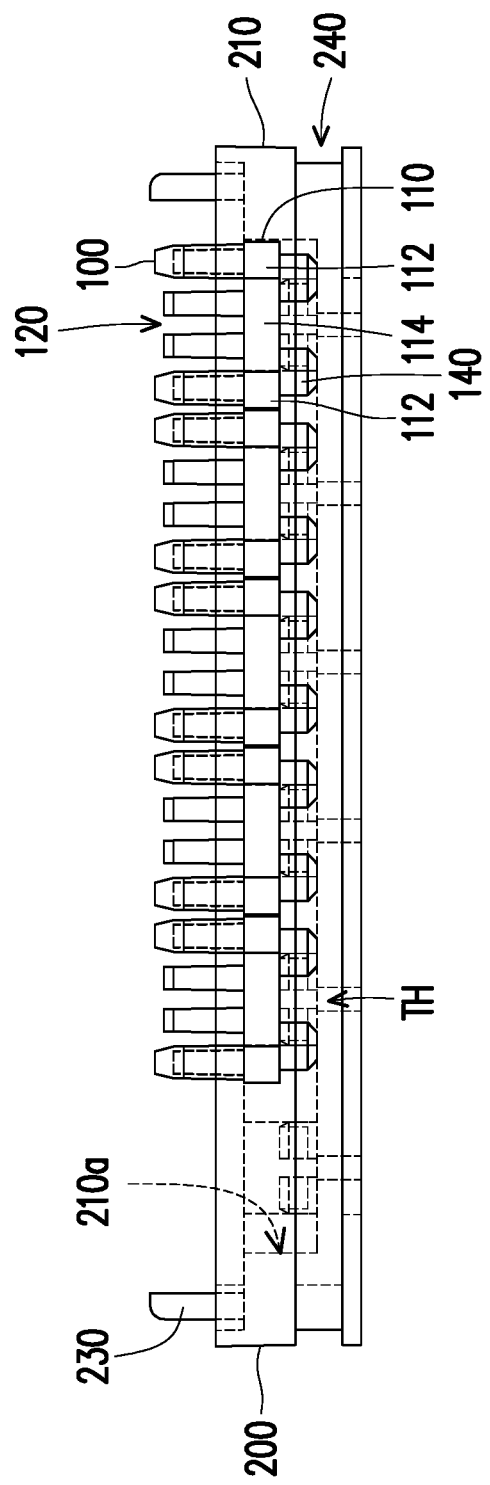
FIG. 2A is a schematic side view illustrating microarray blocks assembled to a block holder according to an embodiment of the disclosure.
Figure 2B:
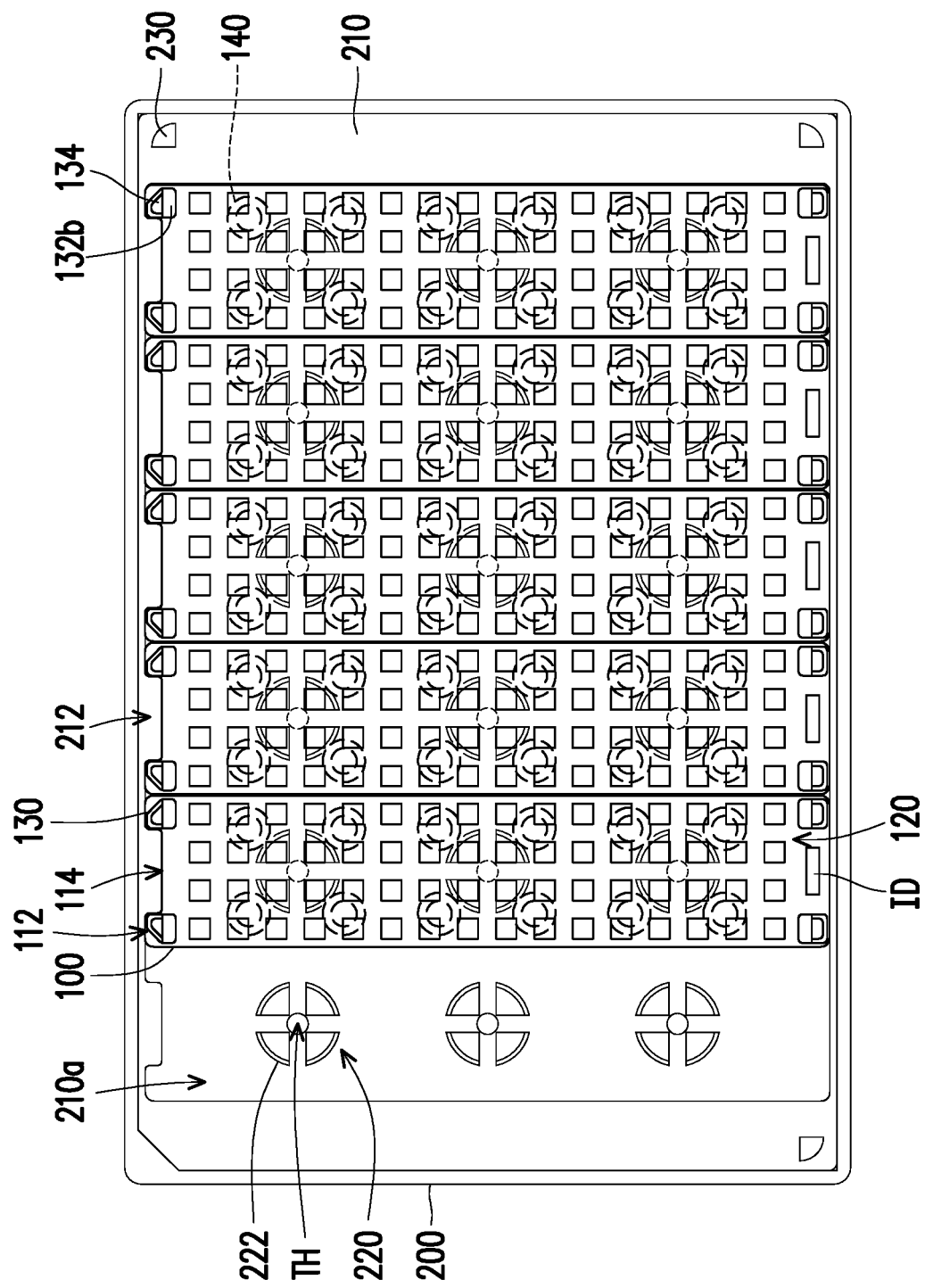
FIG. 2B is a schematic top view of FIG. 2A according to an embodiment of the disclosure.

FIG. 1A is a schematic exploded side view of a microarray carrier assembly according to an embodiment of the disclosure, FIG. 1B is a schematic cross sectional view of the dashed box A indicated in FIG. 1A along a length direction of a microarray block according to an embodiment of the disclosure, FIG. 2A is a schematic side view illustrating microarray blocks assembled to a block holder according to an embodiment of the disclosure, and FIG. 2B is a schematic top view of FIG. 2A according to an embodiment of the disclosure. The drawings in the disclosure are presented as see-through views, and some of dashed lines represent the structures formed or disposed inside the objects. Referring to FIG. 1A to FIG. 2B, a microarray carrier assembly 10 includes at least one microarray block 100. In some embodiments, the microarray carrier assembly 10 further includes a block holder 200, and the microarray block 100 may be detachably disposed on the block holder 200 such that the block holder 200 carries the microarray block 100. In some embodiment, the block holder 200 can be omitted, and the detailed description will be described later in other embodiments. It should be noted that the numbers of the microarray block 100 disposed on the block holder 200 shown in the drawings merely serves as an exemplary illustration, and the vacancy of the block holder (e.g., shown in FIG. 2A and FIG. 2B) for accommodating the microarray block is for the purpose to show the interior structure of the block holder without the microarray block, and such vacancy can be filled by the microarray block, or the block holder can have more vacancy and carry less microarray block based on demand.

For example, the microarray block 100 includes a main body 110, a probe array 120, a guiding pin 130 and an engaging element 140. The main body 110 has a first side S1 and a second side S2 opposite to the first side S1. The probe array 120 is distributed on the first side S1 of the main body 110, and the guiding pin 130 is disposed on a periphery of the first side S1 of the main body 110. The engaging element 140 is disposed on the second side S2 of the main body 110. The numbers of the guiding pin 130 can be more than one. For example, several guiding pins 130 can be disposed on the main body 110 surrounding the probe array 120 for positioning, and the details will be described later accompanied with figures. In some embodiments, the probe array 120 includes a plurality of pillars 122 arranged in an array, and each pillar 122 includes a biochip 124 bonded thereon. In other words, varying numbers of biological probes can be prepared and immobilized to the pillars 122, thus each pillar 122 may function as a microarray of biological probe. For example, each pillar 122 may have a square cross-section on top uniformly spaced in two adjacent pillars. In some other embodiments, each pillar 122 can have the same or different cross-sectional shapes, such as circular, oval, polygonal, etc.

It should be noted that FIG. 2B showing 64-array format microarray block 100 (e.g., each microarray block 100 is comprised of 64 pillars in a rectilinear array) only serves as an exemplary illustration. The numbers and configurations of the pillars 122 of each microarray block 100 can be customized. For example, the probe array 120 may be configured as 24-array format, 48-array format, 96-array format, more or less. Other amounts, dimensions, shapes and spacing of the pillars 122 may be utilized to form the probe array 120 within the bounds of the disclosure. In some embodiments, multiple microarray blocks 100 can be assembled to the block holder 200 depending on the requirements to obtain customized and high density of microarrays. In some embodiments, each of the microarray blocks 100 may have its own assay format, and multiple microarray blocks 100 arranged in parallel allow for multiplexing a large number of assays. In other words, several microarray blocks 100 having a large variety of biological probes under a multitude assays can be carried by a single block holder 200.

Continue to FIG. 1A, in some embodiments, a top surface area A1 of the guiding pin 130 opposite to the main body 110 is less than a bottom surface area A2 of the guiding pin 130 connected to the main body 110. For example, the guiding pin 130 includes a pin body 132 and a footing portion 134 connected to the pin body 132. For example, the pin body 132 includes a first end 132a connected to the main body 110, and a second end 132b opposite to the first end 132a. The footing portion 134 of each guiding pin 130 may extend from the second end 132b of the pin body 132 along a height direction D of the guiding pin 130, and thus each guiding pin 130 has a maximum height MH1 combining a height of the footing portion 134 and a height of the pin body 132; that is, the maximum height MH1 is measured from the top surface of the footing portion 134 to the surface the first end 132a. In some embodiments, the size of the footing portion 134 may be smaller than the size of the pin body 132. The top surface area A1 is the top surface of the footing portion 134, and the bottom surface area A2 may be equal to the surface area of the first end 132a or the surface area of the second end 132b.

The dashed box A shown in FIG. 1B is a schematic cross sectional view of a portion of the microarray block 100 along a length direction of a microarray block. Referring to the dashed box A in FIG. 1B, each pillar 122 has a height H2 measured from the surface connected to the main body 110 to the surface bonded to the biochip 124. In some embodiments, a height H1 of the pin body 132 measured from the first end 132a to the second end 132b is less than a height H2 of the probe array 120. In some embodiments, the maximum height MH1 is greater than a total height of the height H2 of the pillar 122 combining with the thickness of the biochip 124. In some embodiments, each of the guiding pins 130 includes an L-shaped surface LS defined by a lateral surface LS1 of the footing portion 134 and a surface LS2 of the second end 132b of the pin body 132 exposed by the footing portion 134. For example, the surface LS2 of the second end 132b is substantially perpendicular to the lateral surface LS1 of the footing portion 134. The footing portion 134 of the guiding pin 130 may be in the form of a truncated cone (e.g., narrow at the top and wide at the bottom) as shown in FIG. 2B. The guiding pins 130 surrounding the probe array 120 may be in the same or different forms depending on the design requirements. In some alternative embodiments, the size of the pin body 132 is substantially equal to that of the footing portion 134. For example, the surface LS2 of the second end 132b is completely covered by the footing portion 134, and the sidewall of the pin body 132 is substantially aligned with that of the footing portion 134.

In some embodiments, each microarray block 100 can be engaged with the block holder 200 through the engaging element 140 (e.g., bumps, protrusions, etc.). For example, the block holder 200 may include a housing 210 having a recess 210a, and a plurality of engaging units 220 disposed within the recess 210a. The recess 210a of the housing 210 may serve as the accommodating space, so that the microarray blocks 100 can be assembled into the recess 210a of the housing 210 and detachably engaged with the block holder 200 through the engaging units 220. In some embodiments, each engaging unit 220 includes a plurality of sub-engaging members 222 distributed on the surface of the recess 210a, and an engaging area may be defined by the sub-engaging members 222. In some embodiments, when the microarray block 100 is disposed on the block holder 200, the plurality of engaging elements 140 of each microarray block 100 are disposed surrounding the engaging area and physically abutted to the edges of the sub-engaging members 222 of one of the engaging units 220 as shown in FIG. 2B such that each of the microarray block 100 is firmly engaged with the block holder 200, and the probe arrays 120 of the microarray blocks 100 faces outwardly opposite to the block holder 200. In some alternative embodiments, the engaging elements 140 of the microarray blocks 100 may be recesses, and the engaging units 220 of the block holder 200 may be protrusions in form of complementary shape with the engaging elements 140 such that when the microarray blocks 100 are assembled to the block holder 200, the engaging elements 140 of the microarray blocks 100 can be stably engaged with the engaging units 220 of the block holder 200. However, the configurations, shapes, or forms of the engaging elements 140 of the microarray blocks 100 and the engaging units 220 of the block holder 200 construe no limitation in the disclosure, as long as the microarray blocks 100 can be stably carried by the block holder 200 during transferring or processing.

Continue to FIG. 2B, in some embodiments, each microarray block 100 includes an identification tag ID disposed on the periphery of the main body 110. The identification tag ID may include Radio Frequency Identification (RFID) tag, barcode, QR code, or the like. For example, the identification tag ID is embedded at the periphery of the first side S1 (i.e. same side with the probe array 120). In some embodiments, the identification tag ID can be disposed in the area between the guiding pins 130 where the probe array 120 is blank in such area. In some other embodiments, the identification tag ID is configured at the periphery of the second side S2 (i.e. opposite side with the probe array 120) or the lateral surface of the main body 110 connected to the first side S1 and the second side S2. For example, each microarray block 100 can be used to perform different assays, and the detailed information (e.g., assay contents, lot number, date of manufacture, expiration date, number of microarray chips, manufacturer, user ID, etc.) of each microarray block 100 can be recorded in the identification tag ID.

Still referring to FIG. 2A and FIG. 2B, in some embodiments, each microarray block 100 includes a convex portion 112 and a concave portion 114 connected to the convex portion 112 at the periphery of the main body 110. For example, the guiding pins 130 are disposed on the convex portion 112 of the main body 110. In some embodiments, the convex portion 112 and the concave portion 114 may be disposed at one side of the periphery of the main body 110, and the opposite side of the periphery of the main body 110 may be or may be not disposed the convex portion 112 and the concave portion 114. In certain embodiments, the convex portion 112 and the concave portion 114 are disposed at only one side and without disposing at the opposite side, then the convex portion 112 and the concave portion 114 may function as the distinguishing features of the orientation of each microarray block 100, thereby facilitating assembling the microarray blocks 100 to the block holder 200. In some embodiments, the housing 210 of the block holder 200 may include a protrusion portion 212 disposed at the periphery of the recess 210a of the housing 210 and complementary in shape with the concave portion 114 of the microarray block 100. When the microarray blocks 100 are assembled to the block holder 200, the concave portion 114 at the periphery of the main body 110 of each microarray block 100 and the protrusion portion 212 at the periphery of the block holder 200 may be interfittingly engaged.

Continue to FIG. 1A and FIG. 2A, in some embodiments, the block holder 200 further includes at least one buffer pin 230 disposed at the periphery of the housing 210 outside the recess 210a. For example, after the microarray blocks 100 are assembled to the block holder 200, a height of the buffer pin 230 of the block holder 200 is greater than the maximum height MH1 of each guiding pin 130 of the microarray block 100 so as to prevent the biochips 124 of the microarray block 100 from contamination. In some embodiments, a lateral trench 240 may be optionally disposed along the sidewall of the housing 210 of the block holder 200. For example, the lateral trench 240 of the block holder 200 may allow the compatible automatic robotic system for transferring the block holder 200 with the microarray blocks 100 assembled thereon. However, the configuration and the form of the lateral trench 240 may depend on the requirement of the compatible automatic robotic system, which is not limited thereto.

Figure 3:
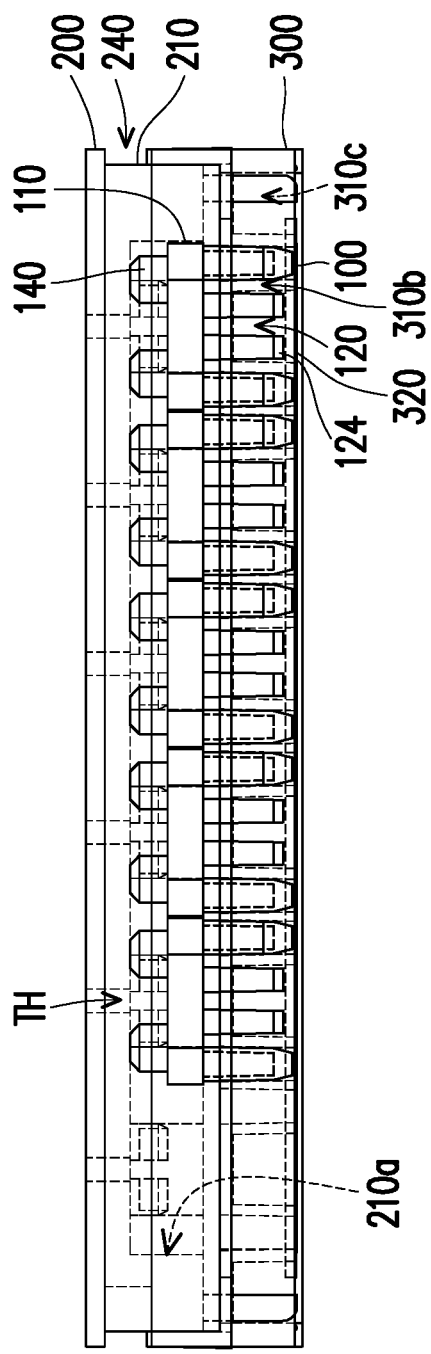
FIG. 3 is a schematic side view illustrating the assembly shown in FIG. 2A being disposed on a scan tray according to an embodiment of the disclosure.

FIG. 3 is a schematic side view illustrating the assembly shown in FIG. 2A being disposed on a scan tray according to an embodiment of the disclosure. Referring to FIG. 1A to FIG. 3, for example, the microarray carrier assembly 10 includes the microarray block 100 and a scan tray 300. In some embodiments, the scan tray 300 includes a frame 310 and a transparent substrate 320. For example, the frame 310 includes an opening 310a, a slot 310b, and a pin hole 310c. The transparent substrate 320 may be disposed on the frame 310 to cover the opening 310a. In some embodiments, the frame 310 may have a plurality of the slots 310b, and the number of the slots 310b may correspond to that of the guiding pins 130 of the microarray blocks 100. The slots 310b may be disposed at the periphery of the frame 310 and surround the opening 310a. The number and the shape of the pin holes 310c may correspond to that of the buffer pins 230 of the block holder 200 for engaging with one another, and the pin holes 310c may be disposed at the periphery of the frame 310 and surround the opening 310a. For example, the size of the transparent substrate 320 and the size of the opening 310a of the frame 310 may match to each other. In some embodiments, the size of the transparent substrate 320 may be greater than that of the opening 310a. For example, a protruded portion 320a at the periphery of the transparent substrate 320 may be attached to the frame 310 through a glue layer 315 (shown in FIG. 5B and FIG. 5C). The protruded portions 320a of the scan tray 300 may correspond to the concave portions 114 of the microarray blocks 100.

Continue to FIG. 3, after the microarray blocks 100 are assembled to the block holder 200, then the microarray blocks 100 carried by the block holder 200 may be flipped over and positioned to the scan tray 300. For example, the guiding pins 130 of the microarray blocks 100 and/or the buffer pin 230 of the block holder 200 can be used to guide the microarray blocks 100 to align the scan tray 300.

Subsequently, the microarray blocks 100 carried by the block holder 200 may be unloaded and disposed on the scan tray 300 so that the biochips 124 of the microarray blocks 100 can face towards the transparent substrate 320 of the scan tray 300 for scanning. For example, the footing portions 134 of the guiding pins 130 of the microarray blocks 100 are positioned to the slots 310b of the frame 310, and then the footing portions 134 of the guiding pins 130 are detachably inserted into the slots 310b of the frame 310 of the scan tray 300. In some embodiments, the biochips 124 may be disposed on a level plane of the probe array 120 and the exposed surfaces of the biochips 124 disposed on the pillars 122 may be leveled. After disposing the microarray blocks 100 on the scan ray 300, the exposed surfaces of the biochips 124 of the probe array 120 of the microarray blocks 100 and a surface of the transparent substrate 320 of the scan tray 300 may be very close to each other or closely attached to each other through water (not shown).

Figure 4:
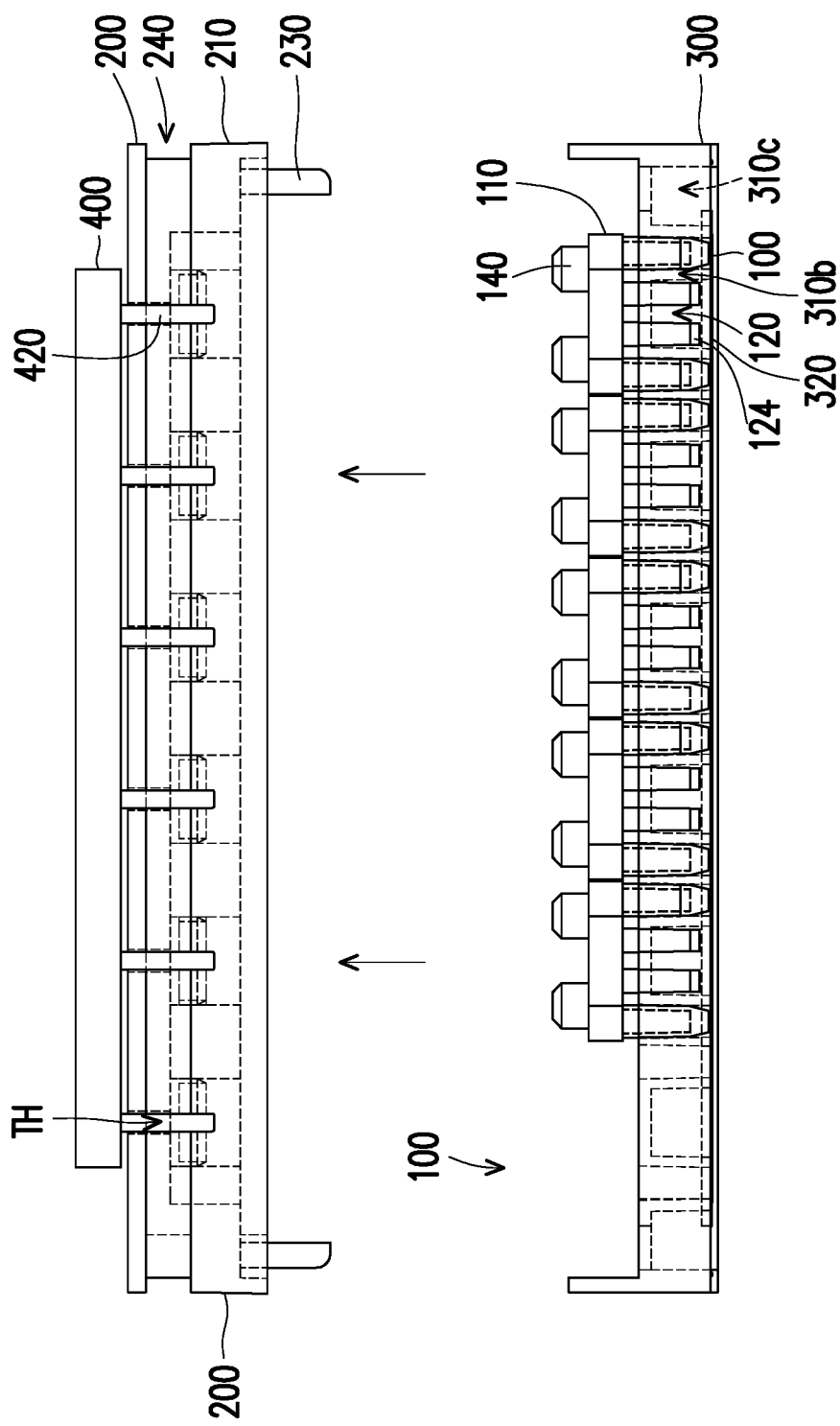
FIG. 4 is a schematic side view illustrating microarray blocks being separated from a block holder by an unloading plate to dispose on a scan tray according to an embodiment of the disclosure.

FIG. 4 is a schematic side view illustrating microarray blocks being separated from a block holder by an unloading plate to dispose on a scan tray according to an embodiment of the disclosure. Referring to FIG. 1A to FIG. 3 and FIG. 4, for example, the microarray carrier assembly 10 may further include an unloading plate 400 in certain embodiments using the block holder 200 to transfer the microarray blocks 100. In some embodiments, the unloading plate 400 includes a plate 410, and at least one unloading pin 420 disposed on the plate 410 and extending along the height direction D. The block holder 200 may include a plurality of through holes TH penetrating through the housing 210, and each through hole TH may be disposed in the engaging area of one of the engaging units 220. In some embodiments, the engaging elements 140 of the microarray blocks 100 may correspond to at least one of the through holes TH of the block holder 200. In other words, when the microarray block 100 is engaged with the block holder 200, each through hole TH is surrounded by the plurality of engaging elements 140 abutted to the sub-engaging members 222 as shown in FIG. 2B. In some alternative embodiments, the height of the engaging elements 140 of the microarray blocks 100 may be substantially equal to that of the sub-engaging members 222, such that the second side S2 of the main body 110 is in contact with the bottom surface of the recess 210a of the block holder 200.

The width (e.g., diameter) of the unloading pin 420 may be equal or smaller than the width (e.g., diameter) of the through hole TH of the block holder 200. The length of the unloading pin 420 of the unloading plate 400 may be greater than the depth of the through hole TH of the block holder 200. The number of the unloading pins 420 may correspond to that of the through holes TH such that the microarray blocks 100 can be detached from the block holder 200 at one time using the unloading plate 400. For example, the user can manually or control the compatible automatic robotic system (not shown) to have the unloading pins 420 of the unloading plate 400 positioned to the through holes TH of the block holder 200, and then have the unloading pins 420 penetrating through the through holes TH to reach the second sides S2 of main bodies 110 of the microarray blocks 100. The user may push the unloading plate 400 to have the unloading pins 420 completely passing the through holes TH so as to force the microarray blocks 100 separate from the block holder 200. Thereafter, the buffer pins 230 of the block holder 200 may be pulled out from the pin holes 310c of the scan tray 300, and then the microarray blocks 100 are detached from the block holder 200 and left on the scan tray 300.

In some alternative embodiment, the block holder 200 and the unloading plate 400 can be omitted, and a user can manually dispose the microarray blocks 100 on the scan tray 300 with the biochips 124 facing towards the transparent substrate 320 of the scan tray 300 for scanning.

Figure 5A:
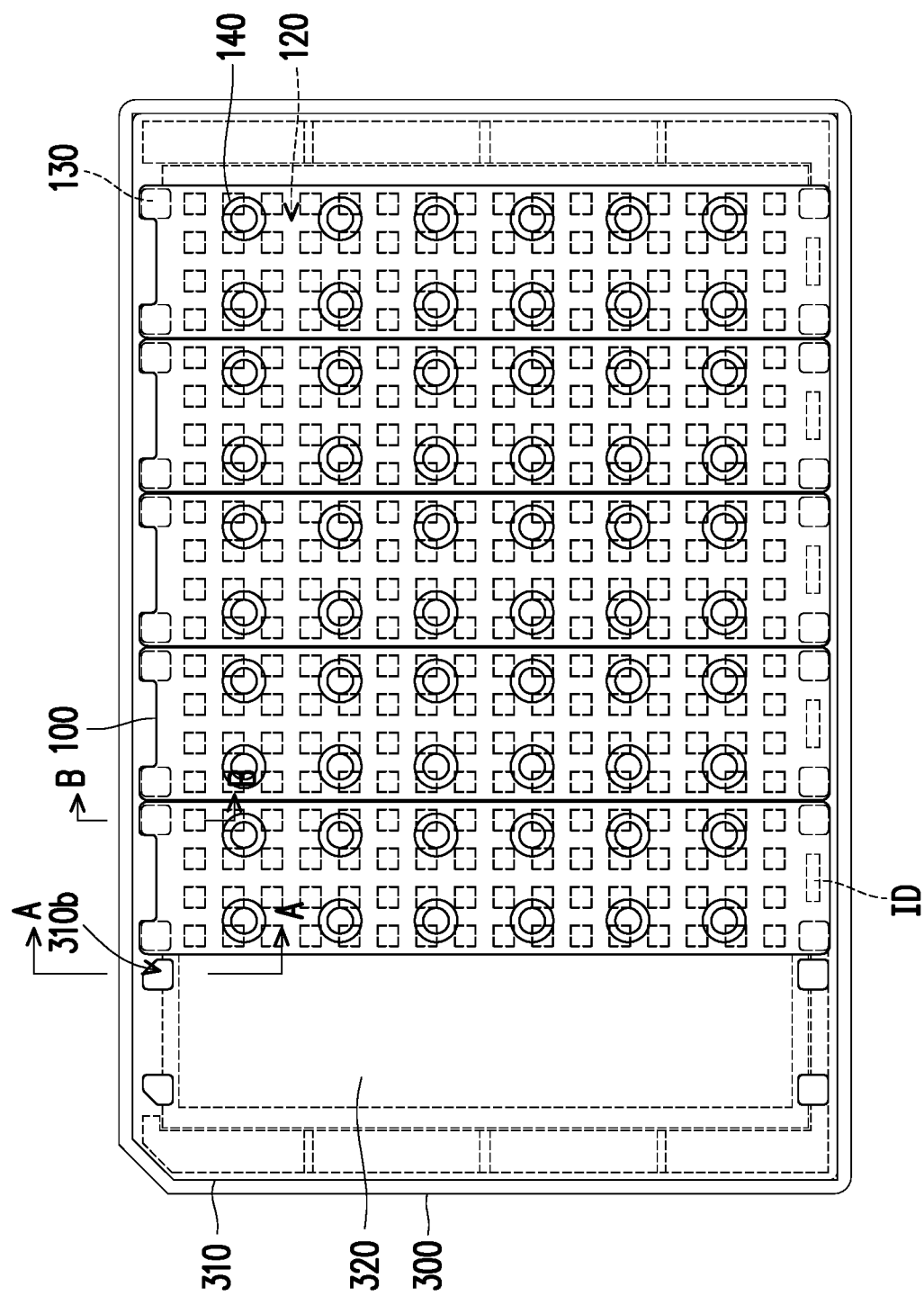
FIG. 5A is a schematic top view illustrating microarray blocks disposed on a scan tray according to an embodiment of the disclosure.
Figure 5C:
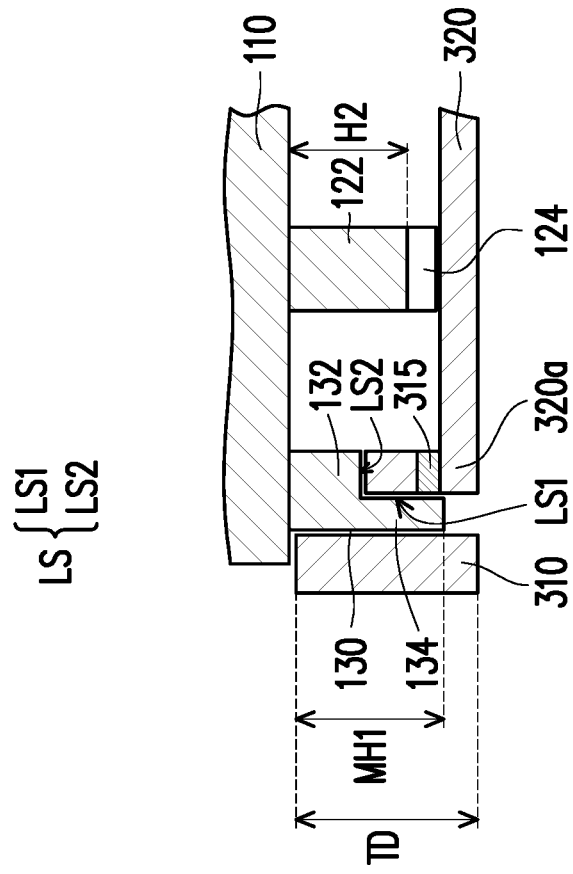
FIG. 5B and FIG. 5C are schematic cross sectional views taken along A-A line and B-B line respectively.
Figure 5B:
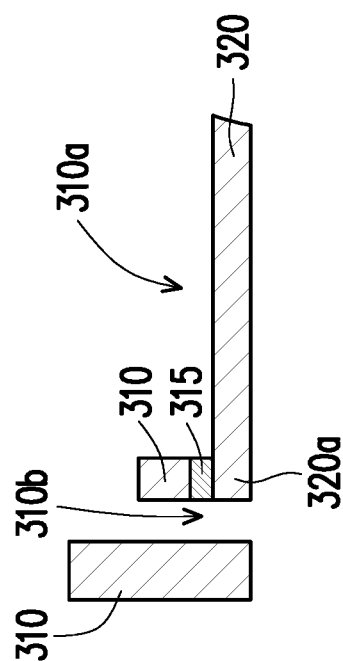

FIG. 5A is a schematic top view illustrating microarray blocks disposed on a scan tray according to an embodiment of the disclosure, and FIG. 5B and FIG. 5C are schematic cross sectional views taken along A-A line and B-B line respectively. Referring to FIG. 1A, FIG. 4 and FIG. 5A, after the block holder 200 is removed and the microarray blocks 100 are disposed on the scan tray 300, the biochips 124 of the microarray blocks 100 facing towards the transparent substrate 320 are ready for assay reading equipment to process. In some embodiment, an array reading system (not shown) may perform optical scanning and interrogate the biochips 124 on the probe arrays 120, thereby obtaining the results of the test. Each of the microarray blocks 100 can also be identified by the array reading system by scanning the identification tag ID.

Continue to FIG. 5A to FIG. 5C, in some embodiments, the L-shaped surfaces LS of the guiding pins 130 of the microarray blocks 100 correspond to the sidewall slot 310b of the frame 310 of the scan tray 300. In some embodiments, the L-shaped surfaces LS of the guiding pins 130 may be spatially apart from the sidewall of the slot 310b of the frame 310; that is, the guiding pins 130 are not in physical contact with the frame 310. In some alternative embodiments, each of the slots 310b may include a complementary profile with the shapes of the footing portions 134 of the guiding pins 130 so that when the guiding pins 130 are inserted into the slots 310b, the profile inside the slots 310b may engage with or stuck the footing portions 134, and the lateral surface LS1 and/or the surfaces LS2 of the second ends S2 of the pin body 132 exposed by the footing portions 134 may be in physical contact with the frame 310 of the scan tray 300. In other words, the footing portions 134 of the guiding pins 130 inserted into the slots 310b of the frame 310 may be or may not be in physical contact with the surface of the slots 310b depending on the size (e.g., length, width or height) of the slots 310b and/or the size of the guiding pins 130. In some embodiments, a slight gap is between the biochips 124 and the surface of the transparent substrate 320 and such slight gap is filled by water to make the biochips 124 closely attach to the surface of the transparent substrate 320, or no gap is between the biochips 124 and the surface of the transparent substrate 320, for better imaging and easier detection by the array reading system.

For example, the maximum height MH1 of each guiding pin 130 combining with a gap between the top surface of the footing portion 134 and the bottom surface of the slot 310b is referred to as a total depth TD indicated in FIG. 5C. The gap between the top surface of the footing portion 134 and the bottom surface of the slot 310b may be substantially equal to the thickness of the transparent substrate 320 or slightly less than the thickness of the transparent substrate 320. In some alternative embodiments, the gap between the top surface of the footing portion 134 and the bottom surface of the slot 310b may be slightly greater than the thickness of the transparent substrate 320. In some embodiments, a total thickness of a thickness of the transparent substrate 320 and a thickness of the biochip 124 is greater than a first height (the first height is the total depth TD minus the height H2 of the pillar 122). In some embodiments, the first height of the total depth TD minus the height H2 of the pillar 122 is greater than a thickness of the biochip 124. For example, the thickness of each biochip 124 is about 650 μm and the thickness of the transparent substrate 320 is about 1000 μm.

To sum up, since multiple microarray blocks 100 may be used to perform a multitude assays simultaneously, thereby achieving high-volume throughput of different biological samples and improving imaging sensitivity. The microarray carrier assembly includes at least one microarray block detachably disposed on the scan tray. Each microarray block includes a probe array, and the quantity of the probe array can be customized. Moreover, a plurality of microarray blocks can be assembled onto the scan tray and the block holder, and each microarray block can be a different assay such that the scan tray and the block holder carries multiple assays on these microarray blocks. Therefore, the user can run the multiple assays at the same time using these microarray blocks. In addition, the maximum height of the guiding pin is higher than the probe array to prevent contamination. Furthermore, the microarray blocks can be easily separated from the block holder using the unloading plate.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A microarray carrier assembly, comprising:
    a scan tray comprising:
        a frame comprising an opening and a slot; and
        a transparent substrate covering the opening of the frame; and
    a plurality of microarray blocks detachably disposed on the scan tray, each of the microarray blocks comprising:
        a main body;
        a probe array distributed on the main body and facing towards the transparent substrate of the scan tray; and
        a plurality of guiding pins disposed on the main body and surrounding the probe array, wherein a top surface area of the guiding pin opposite to the main body is less than a bottom surface area of the guiding pin connected to the main body, and the guiding pins are detachably inserted into the slot of the frame of the scan tray.

2. The microarray carrier assembly according to claim 1, further comprising a block holder comprising a plurality of through holes, wherein the microarray blocks are detachably disposed on the block holder, and each of the microarray blocks further comprises:
    an engaging element disposed on the main body opposite to the probe array and engaged with the block holder, and the engaging element corresponding to at least one of the through holes of the block holder.

3. The microarray carrier assembly according to claim 2, further comprising:
    an unloading plate comprising a plurality of unloading pins, the unloading pins penetrating through the through holes of the block holder to reach the main bodies of the microarray blocks so as to unload the microarray blocks from the block holder.

4. The microarray carrier assembly according to claim 2, wherein the block holder further comprises:
    a plurality of engaging units detachably engaged with the microarray blocks and each of the engaging units comprising a plurality of sub-engaging members, wherein an engaging area is defined by the sub-engaging members.

5. The microarray carrier assembly according to claim 4, wherein the engaging element of each of the microarray blocks is abutted to the edges of the sub-engaging members of one of the engaging units.

6. The microarray carrier assembly according to claim 4, wherein each of the through holes of the block holder is disposed in the engaging area of one of the engaging units.

7. The microarray carrier assembly according to claim 1, wherein each of the guiding pins comprises:
    a pin body comprising a first end connected to the main body, and a second end opposite to the first end; and
    a footing portion extending from the second end of the pin body along a height direction of the guiding pins, wherein the footing portion is detachably inserted into the slot of the frame of the scan tray.

8. The microarray carrier assembly according to claim 7, wherein the probe array comprises a plurality of pillars arranged in an array, and each of the pillars comprises a biochip bonded thereon, a maximum height of one of the guiding pins combing with a gap between the one of the guiding pins and a bottom surface of the slot minus a height of one of the pillars is a first height, and the first height is greater than a thickness of the biochip.

9. The microarray carrier assembly according to claim 8, wherein a total thickness of a thickness of the biochip combining with a thickness of the transparent substrate of the scan tray is greater than the first height.

10. The microarray carrier assembly according to claim 7, wherein a cross-sectional area of the footing portion is smaller than a cross-sectional area of the pin body.

11. The microarray carrier assembly according to claim 7, wherein a height of the pin body measured from the first end to the second end is less than a height of the probe array.

12. The microarray carrier assembly according to claim 7, wherein each of the guiding pins comprises an L-shaped surface defined by a lateral surface of the footing portion and a surface of the second end of the pin body exposed by the footing portion.

13. The microarray carrier assembly according to claim 1, wherein each of the microarray block further comprises:
    an identification tag disposed on the periphery of the main body.

14. The microarray carrier assembly according to claim 1, wherein the periphery of the main body of each of the microarray blocks comprises a convex portion and a concave portion connected to the convex portion, and the guiding pins are disposed on the convex portion.

15. The microarray carrier assembly according to claim 14, wherein the scan tray further comprises a protruded portion disposed at the periphery of the transparent substrate, and the concave portion of the main body of each of the microarray blocks is complementary in shape with the protruded portion.

16. A microarray carrier assembly, comprising:
    at least one microarray block comprising:
        a main body having a first side and a second side opposite to the first side;
        a probe array distributed on the first side of the main body and including a plurality of pillars and biochips bonded thereon; and
        a guiding pin disposed on a periphery of the first side of the main body; and a scan tray, the at least one microarray block detachably assembled to the scan tray, and the scan tray comprising:
- a frame comprising an opening and a slot; and
- a transparent substrate covering the opening of the frame, wherein the guiding pin of the at least one microarray block is detachably inserted into the slot of the frame, and a maximum height of the guiding pins combing with a gap between the guiding pin and a bottom surface of the slot minus a height of the probe array is a first height, and the first height is greater than a thickness of one of the biochips.

17. The microarray carrier assembly according to claim 16, wherein the at least one microarray block further comprises an engaging element disposed on the main body opposite to the probe array, and the microarray carrier assembly further comprises:
- a block holder detachably engaging with the at least one microarray block via the engaging element and comprising at least one through hole, wherein the engaging element of the at least one microarray block corresponds to the at least one through hole.

18. The microarray carrier assembly according to claim 17, further comprising:
- an unloading plate comprising at least one unloading pin, the at least one unloading pin penetrating through the at least one through hole of the block holder to reach the main body of the at least one microarray block so as to unload the at least one microarray block from the block holder.

19. The microarray carrier assembly according to claim 16, wherein a total thickness of a thickness of the biochip combining with a thickness of the transparent substrate of the scan tray is greater than the first height.

20. The microarray carrier assembly according to claim 16, wherein the guiding pin of the at least one microarray block comprises:
- a pin body having a first end connected to the first side of the main body and a second end opposite to the first end; and
- a footing portion extending from the second end of the pin body along a height direction of the guiding pin, wherein the footing portion is detachably inserted into the slot of the frame of the scan tray, and the pin body and the footing portion is spatially apart from the slot of the scan tray.

* * * * *